United States Patent [19]

Bragdon et al.

[11] 3,987,077

[45] Oct. 19, 1976

[54] COMPOSITION USEFUL FOR REDUCING THE CAKING TENDENCY OF PARTICULATE SODIUM CHLORIDE

[75] Inventors: Robert Wright Bragdon, Marblehead, Mass.; Jon Carl Thunberg, Amherst, N.H.

[73] Assignee: W. R. Grace & Co., New York, N.Y.

[22] Filed: June 16, 1975

[21] Appl. No.: 586,940

[52] U.S. Cl. ............................ 260/465.5 R; 423/268
[51] Int. Cl.² ........................................ C07C 121/43
[58] Field of Search .............. 260/465.5 A, 465.5 R, 260/534 E, 561 A

[56] References Cited
UNITED STATES PATENTS

| | | | |
|---|---|---|---|
| 2,855,428 | 10/1958 | Singer et al. | 260/465.5 A |
| 3,409,666 | 11/1968 | Foreman | 260/534 |
| 3,463,811 | 8/1969 | Godfrey et al. | 260/465.5 A |

OTHER PUBLICATIONS

"The Chemistry of the Cyano Group", Edited by Rapoport, 1970, Interscience Publishers, pp. 168–169.
"Handbook of Tables for Organic Compound Identification", 3rd Ed., 1967, Chemical Rubber Co., p. 344.

*Primary Examiner*—Joseph Paul Brust

[57] ABSTRACT

An aqueous solution is prepared by: (a) admixing nitrilotriacetonitrile and aqueous hydrochloric acid to form a first mixture; (b) reacting the nitrilotriacetonitrile and the hydrochloric acid components of the first mixture at 25°–70° C to form a second mixture; and (c) adjusting the pH of the second mixture to about 3–7 by admixing the second mixture and sodium hydroxide, potassium hydroxide, or ammonia to form the aqueous solution. Said solution is useful for reducing the caking tendency of particulate sodium chloride. Said solution is also useful as an additive to systems in which potassium chloride is to be separated from sodium chloride by froth flotation. Said solution is also useful as an inhibitor for inhibiting the crystallization of sodium chloride from brines, including brines encountered in oil well operations.

3 Claims, No Drawings

COMPOSITION USEFUL FOR REDUCING THE CAKING TENDENCY OF PARTICULATE SODIUM CHLORIDE

BACKGROUND OF THE INVENTION

This invention is in the field of nitrilotriacetonitrile (NTAN). More particularly it is in the field of a composition prepared by reacting NTAN with aqueous HCl and then adjusting the pH of the resulting aqueous product to about 3-7 with sodium hydroxide, potassium hydroxide, or ammonia, said composition being useful for reducing the caking tendency of particulate sodium chloride.

U.S. Pat. No. 3,856,922 (Bragdon, 423/268) teaches a method for reducing the caking tendency of sodium chloride and lists prior art methods for reducing the caking tendency of sodium chloride and for modifying its appearance or crystal habit.

SUMMARY OF THE INVENTION

In summary, this invention is directed to a process for preparing a product composition useful for reducing the caking tendency of particulate sodium chloride, said process comprising:

a. forming a first mixture by admixing nitrilotriacetonitrile and an aqueous HCl solution analyzing about 20-42% (preferably about 31-37%) HCl, the nitrilotriacetonitrile and the HCl being admixed in a mole ratio of nitrilotriacetonitrile to HCl of about 1:2-5 (preferably about 1:2.5-3.5) over a period of about 1-24 hours (preferably 2-6 hours) while maintaining the resulting first mixture at about 25°-70° C (preferably 30°-60° C or 30°-40° C);

b. forming a second mixture by adjusting the temperature of the first mixture to about 25°-70° C (preferably about 30°-60° C or 30°-40° C) if it is not already at said temperature, and maintaining the first mixture at said temperature for 1-24 hours (preferably 1-4 hours); and c. forming said product compositions by adjusting the pH of the second mixture to about 3-6 (preferably about 4.5-6) by admixing the second mixture and an amount of sodium hydroxide, potassium hydroxide, or ammonia effective for producing said pH. If too much NaOH, KOH, or $NH_3$ is added (thereby making the pH higher than desired) hydrochloric acid solution can be added to lower the pH of the final product to the desired (or predetermined) value.

Said composition is an aqueous solution.

Sodium hydroxide or potassium hydroxide are preferably added to the second mixture as concentrated aqueous solutions (e.g., an aqueous solution analyzing 20-50% (or 40-50%) NaOH or an aqueous solution analyzing 20-50% (or 30-45%) KOH while agitating the second mixture.

Ammonia can be admixed with the second mixture as liquid anhydrous ammonia, as anhydrous ammonia vapor, or as an aqueous solution of ammonia (e.g., 12-28% or 20-28% $NH_3$).

If a product composition (solution) containing more water than that provided by the aqueous HCl solution is desired, more water can be added to: (a) the aqueous HCl solution; (b) the first mixture; (c) the second mixture; (d) said composition, or (e) to any two or more of (a) through (d).

We generally prefer to use such amounts of water (including any which is added in addition to the water present in the aqueous HCl solution used), HCl, and NTAN such that about 0.5-1.5 (preferably 0.5-1) moles of NTAN will be fed per liter of resulting product composition.

DESCRIPTION OF PREFERRED EMBODIMENTS

In a preferred embodiment ("Embodiment A") this invention is directed to the composition prepared by the process of the above Summary.

In another preferred embodiment ("Embodiment B") this invention is directed to a solid composition, useful for reducing the caking tendency of particulate sodium chloride, prepared by evaporating water from the composition of Embodiment A (e.g., evaporating the composition of Embodiment A to dryness or substantially to dryness).

Such evaporation can be conducted at atmospheric pressure (i.e., 760 mm of mercury absolute), under reduced pressure, or under slightly elevated pressure (e.g., up to about 1.5 atmosphere absolute pressure or somewhat higher). We generally prefer to conduct the evaporation at atmospheric pressure or under a slight vacuum (e.g., 100-500 mm of mercury absolute).

DETAILED DESCRIPTION OF THE INVENTION

To reduce the caking tendency of particulate sodium chloride we prefer to admix about 0.01-1 g of the composition (solution) of our above Embodiment A (or about 0.005-0.5 g of the composition (solid) of our above Embodiment B) with each liter to a solution from which particulate solid sodium chloride is to be crystallized before crystallizing sodium chloride from the resulting mixture.

To facilitate the separation of potassium chloride from sodium chloride by froth flotation we prefer to admix about 0.05-1 g of the composition (solution) of our above Embodiment A (or about 0.025-0.5 g of the composition (solid) of our Embodiment B) with each 1000 kg of the aqueous system from which the potassium chloride is to be separated, and then proceeding with such separation in a conventional manner.

To inhibit the crystallization of sodium chloride from a brine we prefer to admix about 0.01-1 g of the composition (solution) of our above Embodiment A (or about 0.005-0.5 g of the composition (solid) of our above Embodiment B) with each liter of the brine.

The instant invention will be better understood by referring to the following specific but nonlimiting examples and procedures. It is understood that said invention is not limited by these examples and procedures which are offered merely as illustrations; it is also understood that modification can be made without departing from the spirit and scope of the invention.

EXAMPLE 1

A 3,760 lb. portion of 20° Be' hydrochloric acid solution (ca. 32.2% HCl, 32.4 lb. moles of HCl) was placed in a 1,000 gallon glass lined reactor provided with a stirring means, a heating means, inlet and outlet ports, a vent, and a cooling jacket. The temperature of the solution in the reactor was adjusted to 25° C and a 1,250 lb. portion (9.31 lb. moles) of NTAN was added thereto over a period of 3.5 hours while stirring the resulting mixture in the reactor and while maintaining the temperature thereof within a range of 25°-39° C. After all the NTAN had been added the resulting mixture was stirred for an additional 1 hour period while maintaining the temperature thereof at about 25°–26° C to permit the reaction to go to completion.

A 2,610 lb. portion of a 50% sodium hydroxide solution (32.6 lb. moles) was added to the mixture in the reactor while maintaining the temperature of the mixture below 55° C and while stirring the mixture in the reactor. The product was diluted with water to dissolve suspended solids and to adjust the weight of the resulting solution to 9,240 lbs. The thus formed product had a pH of 5.

EXAMPLE 2

The general procedure of Example 1 was repeated. However, in this instance the procedure was modified by: (a) using 2,620 lbs. of 50% sodium hydroxide solution (32.5 lb. moles of NaOH); (b) adding the NTAN over a 4.3 hour period while maintaining the temperature of the mixture in the reactor at 30°–36° C; (c) maintaining the mixture formed by adding the NTAN to the HCl solution at 45° C for 1 hour after all of the NTAN had been added; (d) by adding water to adjust the weight of the product to 8,770 lbs; and (e) then adding 50 lbs. of the 20° Be' hydrochloric acid solution to adjust the pH of the product to 5.5. The final product weighed 8,820 lbs.

EXAMPLE 3

The general procedure of Example 1 was repeated. In this instance, the quantities of reactants used were: 3,760 lbs. of 20° Be' hydrochloric acid solution (32.4 lb. moles of HCl), 1,250 lbs. (9.31 lb. moles) of NTAN, and 2,700 lbs. of 50% sodium hydroxide solution (33.8 lb. moles of NaOH).

The NTAN was added to the hydrochloric acid solution over a period of 4.3 hours while maintaining the temperature of the resulting mixture at about 31°–36° C. After the NTAN had been added the resulting mixture was maintained at 32°–35° C for 2.3 hours. At the end of this time the sodium hydroxide solution was added, over a period of about 2 hours to the above mentioned resulting mixture while agitating the mixture and while maintaining the temperature thereof below 55° C. After all of the sodium hydroxide had been added water was added to adjust the weight of the thus formed product to 9,000 lbs. The thus diluted final product had a pH of 5.

EXAMPLE 4

The general procedure of Example 1 was repeated. However, in this instance the procedure was modified by: (a) using 3,240 lbs. of 20° Be' hydrochloric acid solution (27.9 lb. moles of HCl); (b) 1,625 lbs. (12.1 lb. moles) of NTAN; (c) 2,140 lbs. of 50% sodium hydroxide solution (26.8 lb. moles of NaOH); (d) adding the NTAN to the hydrochloric acid solution over a period of 5.3 hours while maintaining the temperature of the resulting mixture at 30°–36° C; (e) maintaining the mixture formed by adding the NTAN to the hydrochloric acid solution at 30°–35° C for 8 hours; and (f) adding water to adjust the final weight of the product to 8,630 lbs. The pH of the final product was 5.

EXAMPLE 5

The general procedure of Example 1 was repeated. However, in this instance the procedure was modified by: (a) using 3,580 lbs. of 20° Be' hydrochloric acid solution (30.9 lb. moles of HCl); (b) 1,440 lbs. (10.7 lb. moles) of NTAN; (c) 2,400 lbs. of 50% sodium hydroxide solution (30.0 lb. moles of NaOH); (d) adding the NTAN to the hydrochloric acid solution over a period of 4 hours while maintaining the temperature of the resulting mixture at 30°–36° C; (e) maintaining the mixture formed by adding the NTAN to the hydrochloric acid solution at 32°–36° C for 3.3 hours; and (f) adding water to 8,670 lbs. The pH of the final product was 5.5.

PROCEDURE 1

The method of Example 3 can be repeated. However, in this procedure the resulting mixture formed by the reaction of the hydrochloric acid solution and the NTAN can be neutralized with 4,220 lbs. of a 45% potassium hydroxide solution (33.8 lb. moles of KOH) can be used in place of the sodium hydroxide solution used in Example 3. The resulting mixture (the mixture which results on the above addition of the KOH solution) can then be diluted with water to yield 12,000 lbs. of product solution having a pH of 5.

PROCEDURE 2

The general method of Example 3 can be repeated. However, in this instance, the sodium hydroxide solution can be replaced with 575 lbs. (33.8 lb. moles) of anhydrous liquid ammonia. After adding the ammonia, water can be added to dilute the product solution to 8,500 lbs. to form a final product solution having a pH of 5.

As used herein, the term "mole" has its generally accepted definition, a mole of a substance being the amount of said substance which contains the same number of molecules of the substance as there are atoms in 12 grams of pure $^{12}C$.

As used herein, "NTAN" means nitrilotriacetonitrile.

As used herein, the term "g" means gram or grams, and the term "kg" means kilogram or kilograms.

As used herein the term "lb." means pound and the term "lbs." means pounds.

We claim:
1. A composition prepared by a process comprising:
   a. forming a first admixture by admixing nitrilotriacetonitrile and an aqueous hydrochloric acid solution analyzing about 20–42% HCl, the nitrilotriacetonitrile and the hydrochloric acid solution being admixed in a mole ratio of nitrilotriacetonitrile to HCl of about 1:2–5 over a period of about 1–24 hours while maintaining the resulting first admixture at about 25°–70° C;
   b. forming a second admixture by adjusting the temperature of the first admixture to about 25°–70° C if it is not already at said temperature, and maintaining the first admixture at said temperature for 1–24 hours; and
   c. forming said composition by adjusting the pH of the second admixture to about 3–7 by admixing the second mixture and an amount of sodium hydroxide, potassium hydroxide, or ammonia effective for producing said pH.

2. The composition of claim 1 in which the pH of the second admixture is adjusted to about 3–7 by admixing the second admixture and an amount of sodium hydroxide effective for producing said pH.

3. A product prepared by evaporating the composition of claim 1 substantially to dryness.

* * * * *